United States Patent [19]

Armstrong

[11] 4,202,371

[45] May 13, 1980

[54] SYSTEM FOR POLLUTION SUPPRESSION

[75] Inventor: Edward T. Armstrong, Butler, N.J.

[73] Assignee: TII Corporation (Telecommunications Industries, Inc.), Lindenhurst, N.Y.

[21] Appl. No.: 616,487

[22] Filed: Sep. 24, 1975

Related U.S. Application Data

[60] Division of Ser. No. 531,095, Dec. 9, 1974, Pat. No. 3,998,714, which is a continuation-in-part of Ser. No. 355,738, Apr. 30, 1973, Pat. No. 3,853,764, which is a continuation-in-part of Ser. No. 100,333, Dec. 21, 1970, Pat. No. 3,730,881, which is a continuation-in-part of Ser. No. 813,382, Feb. 28, 1969, Pat. No. 3,549,528, which is a continuation-in-part of Ser. No. 362,118, Apr. 23, 1964, abandoned.

[51] Int. Cl.$^2$ .............................................. F16K 19/00
[52] U.S. Cl. ...................... 137/604; 423/210; 210/59; 261/76; 261/78 A; 261/116
[58] Field of Search .............. 423/210, 220, 468, 659, 423/59; 137/602, 604; 261/78 R, 78 A, 76, 116; 239/423.5

[56] References Cited

U.S. PATENT DOCUMENTS

| | | | |
|---|---|---|---|
| 716,248 | 12/1902 | Knietsch et al. | 423/468 |
| 945,143 | 1/1910 | Szamek | 137/604 X |
| 2,331,518 | 10/1943 | Trier et al. | 137/604 X |
| 2,447,123 | 8/1948 | Jones | 261/116 |
| 2,899,971 | 8/1959 | Munter | 137/604 X |
| 3,034,771 | 5/1962 | Harris | 261/116 |
| 3,128,994 | 4/1964 | Hungate | 137/604 X |
| 3,190,284 | 6/1965 | Koepf | 137/604 X |
| 3,368,580 | 2/1968 | Carter | 137/604 X |
| 3,432,264 | 3/1969 | Bostwick et al. | 423/522 |
| 3,470,826 | 10/1969 | Foulds | 137/604 X |
| 3,698,430 | 10/1972 | Van Gasselt | 137/604 |
| 3,727,640 | 4/1973 | Sargeant | 137/604 |
| 3,734,111 | 5/1973 | McClintock | 137/604 X |

*Primary Examiner*—Earl C. Thomas
*Attorney, Agent, or Firm*—Oldham, Oldham, Hudak & Weber Co.

[57] ABSTRACT

An apparatus for the treatment of purification of a fluid by treatment with a treating fluid in a flow pipe. The flow pipe has a flat plate orifice located therein, which orifice has an internal diameter of from about 0.7 to about 0.9 of the internal diameter of the pipe. A vena contracta portion is located in the flow pipe at a distance of from 0.25 to 0.5 pipe diameters downstream from said flat plate orifice. An injection nozzle for introducing the treating fluid into the flow pipe extends through the flat plate orifice with the tip of the injection nozzle being located in the vena contracta portion so that the fluid is thoroughly treated by the treating fluid.

12 Claims, 7 Drawing Figures

SYSTEM FOR POLLUTION SUPPRESSION

CROSS-REFERENCE

This application is a division of application Ser. No. 531,095, filed Dec. 9, 1974, now U.S. Pat. No. 3,998,714, which is a continuation-in-part of application Ser. No. 355,738, filed Apr. 30, 1973, now U.S. Pat. No. 3,853,764, which in turn is a continuation-in-part of application Ser. No. 100,333, filed Dec. 21, 1970, now U.S. Pat. No. 3,730,881, which in turn is a continuation-in-part of application Ser. No. 813,382 filed Feb. 28, 1969, now U.S. Pat. No. 3,549,528, which in turn is a continuation-in-part of application Ser. No. 362,118, filed Apr. 23, 1964 and now abandoned.

BACKGROUND OF THE INVENTION

The present invention relates to the treatment or purification of a first fluid with a second fluid possibly a gas, with the first fluid under turbulent flow conditions in a flow conduit. More specifically, the present invention relates to the purification of a first fluid by a fluid (gas) in a flow conduit wherein turbulent flow exists to achieve thorough mixing or momentum transfer.

Heretofore, fluid phase treatment systems have been utilized in purifying fluids such as liquid or gases. In the purification of a gas by other gases, purification has largely been confined to contact chambers, packed beds and the like. In such systems the treated fluid achieves contact with the treating fluid in the packed bed. Where the active agent for treatment is a gas, it may be dissolved in the treating liquid. Contact is achieved as before. However, direct contact is possible between a treating gas and a treated fluid. Although some purification is obtained, the amount is less desirable.

SUMMARY OF THE INVENTION

It is a basic objective of the present invention to provide a fluid treatment system with a treating gas-phase fluid wherein injection-mixing and contact operations are operated under precisely controlled conditions of flow to maximize contact opportunity and to minimize the necessary concentration of treating fluid (gas) required. The key to achieving these conditions is seen to be: to inject and mix so as to suppress the concentration gradients in the axial and in the angular directions at a point where intense radial mixing is induced by a turbulence-causing device and with a high concentration gradient in the radial direction owing to the coaxial injection of treatment fluid (gas) into the treated fluid (liquid or gas) recognizing that this radial concentration gradient will be attenuated downstream of the injection point within a transition length, a second turbulence-causing device is introduced. This induces intense radial mixing, so suppressing any remaining radial concentration gradient. Where said second turbulence-causing device is a flat plate orifice, a further features comes into play. That is, the flat plate orifice is one of few, if not the only turbulence-causing devices which completely removes the laminar and turbulent boundary layer from the conduit wall mixing it into the main stream of treated fluid flow. From this device, contact at maximum probability of contact between treating fluid and treated fluid may continue for a period dictated by reaction rates. Owing to suppression of concentration gradients and to the intense mixing, the reaction rate will be maximized the contact time and the concentration required for the treating fluid (gas).

Generally, the invention relates to a process for the treatment of a fluid by a treating fluid comprising, adding the fluid to a flow conduit in which the Reynolds number is at least 3,000, and flow conduit having a turbulence-causing device, adding a treating fluid to said fluid channel and exhausting a treated fluid.

For a better understanding of the invention reference should be had to the accompanying drawings wherein.

DEFINITION OF TERMS PSEUDOMONAS, ALCALIGENES, FLAVOBACTERIUM, MICROCOCCUS AND ENTEROBACTERIACEAE

ACTIVATED SLUDGE

All types of bacteria make up activated sludge, however, is usual operation obligate anaerobes will attenuate in number in response to the presence of air. A proteinaceous waste will favor alcaligenes, flavobacterium and bacillus. A carbohydrate waste will proliferate pseudomonas as well.

ANAEROBIC DIGESTERS

The anaerobic digester bacteria include facultative and obligate anaerobes in active metabolism. Dormant aerobic forms may be present, such as spores of fungi. Acid formers are predominantly facultative forms although a few obligate anaerobes have metabolic end products which are acid.

Methane formers are obligate anaerobes, methanobacterium, methanosarcina and methanococcus. In the metabolic pathway to subsequent end products where methane is a precursor, the pathway can be intersected owing to the implied vulnerability of methane formers to oxygen, oxygen-ozone or air. Thus selective disinfection provides a means to inhibit methane formation or to deny a metabolic pathway to succeeding end products where methane is the necessary precursor. With denial of a pathway, an alternative pathway may be stimulated by changing environmental conditions such as by initiating aerobic activity. In this way, methane would not be formed. The source material, carbon dioxide would not be reduced. This is an unnecessary step in waste treatment, since carbon dioxide is a stable end product of aerobic treatment. The hydrogen involved would not be acted upon. It is probably a constituent of formic or acetic acid. Thus, the alternative metabolic pathway opened is that for aerobic microbiological decomposition of acetic acid. Instead of the anaerobic sequence of acetic acid; acetoacetic acid to acetic acid, isopropanol to butyric acid or butanol, and unstable end products of high oxidative demand, this invention develops the aerobic sequence. It is: acetic acid, possible pyruvic acid, oxalcetate, citrate and the citric acid (Krebs) cycle to terminal oxidation.

In a similar way, the anerobic reduction of sulfates by the obligate anaerobe desulfovibrio can be inhibited. Shifting to an aerobic environment denies a pathway to hydrogen sulfide. It has been found that this is readily achieved practically by aeration. Consequences include a marked reduction in objectionable odor and long persistence of aerobic action. The latter case is demonstrable by unexpectedly deferred methylene blue stability tests indicating a delayed shift to products of anaerobic metabolism.

MICROORGANISMS IN WASTE TREATMENT

Trickling Filter. Filter microorganisms reflect the facultative nature of the filter. Predominant are bacteria; aerobic, facultative and anaerobic. Obligate aerobic spore formers, bacillus are easily found in the upper, aerobic plaques. The obligate anaerobe, desulfovibrio can be found in lower levels at the plaque-stone interface where, in usual practice, DO is zero. The majority of bacteria are facultative, living aerobically until DO (dissolved oxygen) zeroes, then anaerobically.

Figure 1:
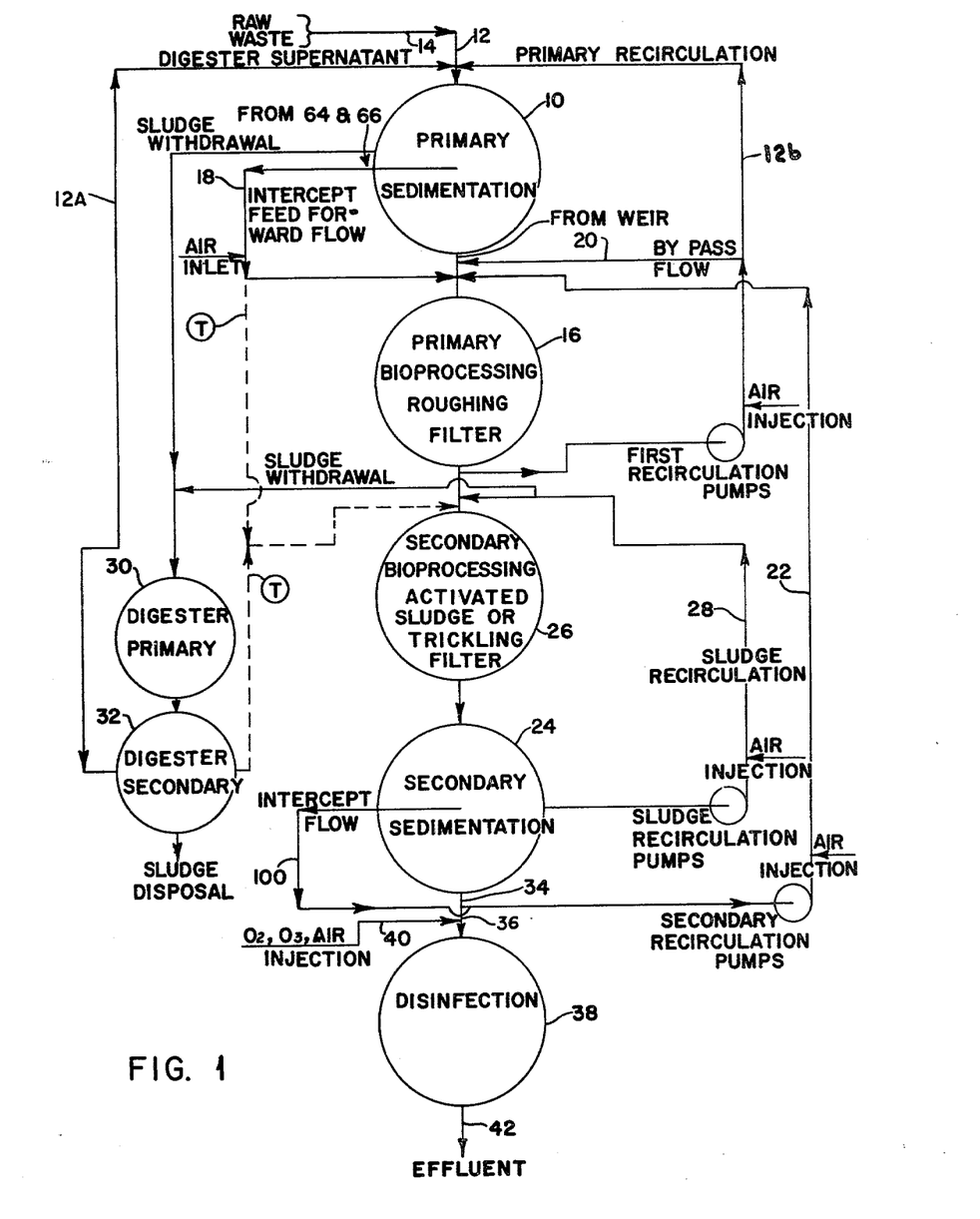
FIG. 1 is a block diagram, schematic illustration of the newly proposed system in total showing flow arrangements and the stages involved.

With reference to the drawings, FIG. 1 illustrates the waste treatment equipment, process and overall system of unit operations in which the invention operates. A primary sedimentation tank is indicated by numeral 10. The tank 10 receives comminuted raw waste including settleable solids from a line 12 issuing from a main line 14. A multiplicity of such lines 12 and subsequent operations may exist.

Two other flows are introduced from the operations which follow, constituting feedback of digester supernatant line 12A and of primary recirculation line 12b. The supernatant fraction is waste having high organic loading, relatively low flow rates, and it is resistant to aerobic processing for two reasons. First, it presents a biotal population adapted to anaerobic digestion and second, its organic composition includes the products of anaerobic metabolism.

The second fraction of flow is the primary recirculation usually occuring at rates in the range of one half to three times the raw waste rate. This recirculation flow is characterized by low organic loading and a high degree of treatability in an aerobic process. It exerts dilution effects on the raw waste which are not only marked, but which may be used in conjunction with secondary recirculation to great advantage in smoothing hydraulic and organic loading, as discussed later.

These three flows are impressed upon primary sedimentation. Regulatory authorities often stipulate hydraulic design criteria for sedimentation equipment in terms of the tank overflow rate which prevails for the composite flow. Such overflow rates may be affected by the technique illustrated in FIG. 1 of intercepting a portion of flow to be fed forward to bioprocessing indicated by numeral 16. As discussed later, in settling, using feed forward techniques, additional benefits accrue for example in organic load smoothing.

The basic flow from primary sedimentation 10 proceeds to a primary stage of bioprocessing 16. A roughing trickling filter is illustrative. There, to the sedimented basic flow, three component flows may be added. One 18 is the feed forward intercept flow noted previously. The second 20 is the bypassing fraction of primary recirculation. The third 22 is the secondary recirculation shown in FIG. 1. The existence of the feedback flows, the feedforward flow and the basic influent flow prior to bioprocessing is important. This combination provides sufficient degrees of freedom to enable independent regulation in this and succeeding operations of hydraulic and organic loading with some flexibility and without overloading primary sedimentation hydraulically. From the bioprocessing operation 16, such as the roughing filter shown, in most cases, existing plant flow proceeds to secondary sedimentation 24. In some instances, a second stage of bioprocessing 26 may be present. Usually this would be a finishing trickling filter. Rarely, but preferably, it would be an activated sludge stage of bioprocessing.

In this instance, as shown in FIG. 1, from the first stage of bioprocessing 16, the flow is split, with primary recirculation over line 12b withdrawing a fraction for feedback to an earlier stage of processing 10. The remaining fraction proceeds to the second stage of bioprocessing 26. Before introduction to bioprocessing 26, such as to the activated sludge operation, it may be mixed with recirculating activated sludge from line 28.

A remaining portion of the recirculating activated sludge is discharged for digestion with the primary sedimentation tank sludge in a primary digester 30 and secondary digester 32.

From the activated sludge operation 26, the flow proceeds to secondary sedimentation 24. The regulatory authorities stipulation on overflow rate again prevails; however, the permissible overflow rate for secondaries 24 may differ for those from primaries and may further depend upon the type of bioprocessing operation involved. The activated sludge operation is characterized by highrates of recirculation over line 22 of sedimented sludge as suggested in FIG. 1.

From the secondary sedimentation operation 24, flow may be intercepted via 100 for feedback recirculation over line 22 after partial sedimentation. A second fraction of fully sedimented flow may be returned in the basic secondary recirculation by line 34. The remaining fully sedimented flow proceeds to disinfection over line 36. In the disinfection unit 38 operation, in-line gas-liquid disinfection over line 40 by injection may precede the conventional contact chamber of disinfection. The technique of gas injection is more fully defined hereinafter. The same, or complementary disinfectants may be used. For example, in-line ozonation might be followed by contact chamber chlorination in unit 38. Alternatively, chlorination may occur in both stages or only in the contact chamber with no in-line disinfection. Disinfection yields the final effluent over line 42.

It has been shown in FIG. 1 that sludge is removed from waste at successive stages of waste treatment. The sludge is stabilized, usually in two-stage anaerobic digesters 30 and 32. From the digester 32, stabilized sludge may be discharged to drying on beds, in a kiln, fluidized bed reactor or may be dewatered, on a vacuum dewatering drum. Ultimate disposition of solid products may be land fill or incineration. Disposition of digester supernatant or of centrate or filtrate over line 12A has been noted previously. It is this overall framework of unit operations within which the concepts proposed by the invention must be implemented. Discussion will now proceed in terms of each of the unit operations described. A later section will deal with optimum systems integration.

It should be noted however that aeration or other injections may take place at a considerable number of other points into the effluent in the system of FIG. 1.

Specifically air may be injected into the digester supernatant recirculation, the raw waste input, the effluent from disinfection tank 38 and to the effluent from the secondary bioprocessing tank 26. In some instances, it is desirable to inject a chlorine water solution into the effluent before disinfection to obtain break point chlorination. It should further be understood, of course, that chlorination may be used in the disinfection tank 38.

FLUID-FLUID TREATMENT

According to the concepts of the present invention, a fluid but desirably a gas can also be treated or purified by treatment with fluid under conditions of high turbulence, that is, a Reynolds number of at least 3,000, to ensure adequate mixing or momentum transfer. In general, a high-turbulence purification treatment may pertain to generally any type of gas although it is particularly suited in the purification of ozone as utilized in treatment of waste treatment facilities as well as sulfur dioxide.

Figure 5:
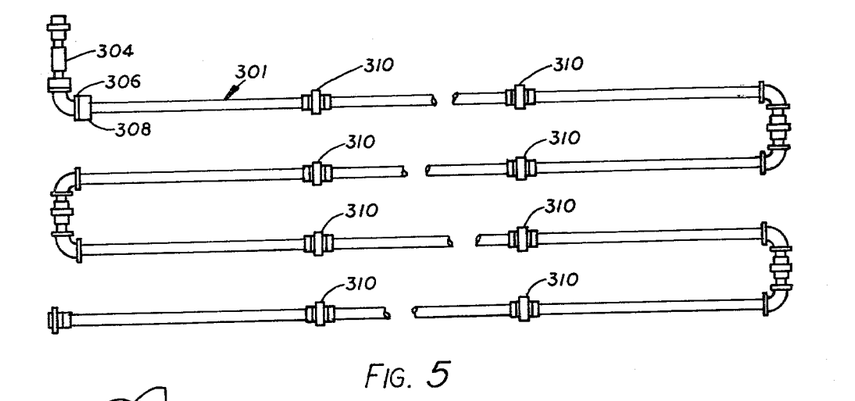
FIG. 5 is a cross-sectional view of a highly efficient fluid-fluid treatment system utilizing high turbulence-causing devices.
Figure 6:
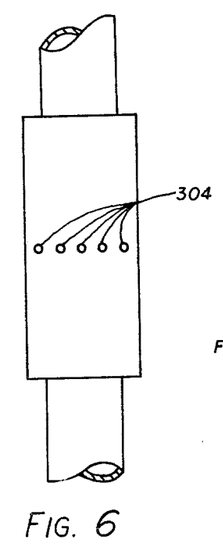
FIG. 6 is a schematic view showing a grid located in a portion of the fluid-fluid treatment system.

Referring to FIG. 5, purification or treatment of a gas may be carried out in a flow or conduit, preferably circular, as in a pipe line, generally indicated by the numeral 301. The gas is admitted to the flow channel as indicated by the arrow and is conveyed through the channel and exhausted. It is highly desirable that the Reynolds number be in excess of 3,000 to ensure turbulent conditions throughout. Preferably, to ensure that a reproducible velocity profile is maintained when beginning the treatment, the grid 304, as shown in FIG. 6, exists to suppress any velocity gradients within the incoming gas. Typically, the grid may be made of wire, plastic, or the like and may be a coarse screen. For example, it may merely be a screen grid with members on approximately one-inch centers of coarse wires having a diameter of approximately 1/16 of an inch. Of course, the size of the grid and wires may vary. The important factor is that a grid may be utilized which ensures the reduction of any velocity gradients. These gradients are likely to be found in discharge sections of fans, blowers, and fittings such as elbows.

Located downstream of grid 304 is a high-turbulence causing device such as a flat plate orifice indicated by the numeral 306 and described herein. Generally, the turbulence causing device can be located at an elbow, union, tee or the like as previously noted. Preferably, the treating fluid is injected into the vicinity of the orifice so that rapid and thorough mixing quickly takes place. Desirably, this can be accomplished through a nozzle 308 which extends axially into the central coaxial portion of the flat plate orifice or turbulence causing device and slightly downstream as in the vena contracta caused by the orifice. Generally, the orifice diameter ranges from about 0.7 to about 0.9 of the conduit diameter. The orifice is located at a distance of 0.25 to 0.5 conduit diameters downstream from the orifice plate, preferably at 0.37 to 0.39 and it is at this region where the nozzle is preferably located. To further ensure thorough and complete mixing, at least one or a second turbulence causing device may be identical to the first device and preferably is located downstream at least a distance of 25 to 40 conduit diameters or greater and preferably at least 40 diameters. This is to ensure that a proper length exists for adequate or thorough mixing. The second turbulence causing device further ensures thorough mixing and hence derives the maximum contact probability for efficient purification of the gas. The treated or purified gas may then be handled in any conventional manner such as by extended contact possibly followed by exhausting to the atmosphere, by recirculation, or by the addition to a process or the like.

Figure 2:
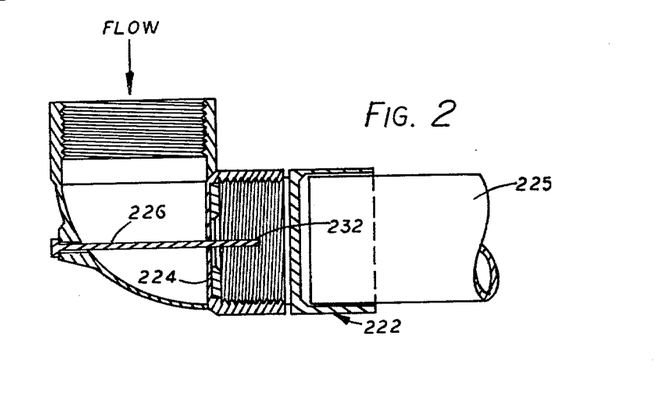
FIG. 2 is a cross-sectional view of an injection mixing elbow.
Figure 3:
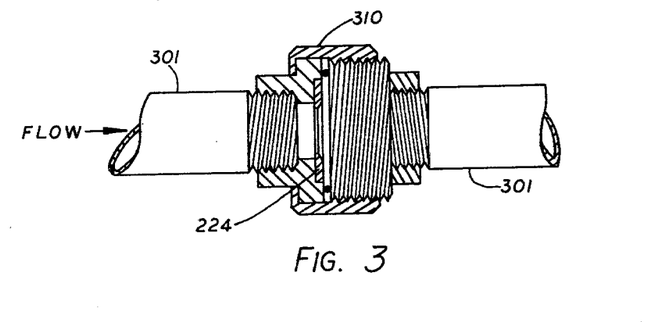
FIG. 3 is a cross-sectional view of a union containing an orifice.

Another example of a high turbulence causing device is shown in FIGS. 2 and 3. In FIG. 2, an injection mixing elbow generally indicated by the numeral 222 having an orifice 224 is located with the elbow at the commencement of the radius. A pipe 225 is attached to the elbow in any conventional manner. A small diameter pipe or tube 226 is inserted through the elbow and through the orifice 224 so that the tip 232 is located within the high turbulence and desirably at or near the vena contracta portion downstream of which full mixing occurs within the flow line or pipe generally indicated by the numeral 225.

The location of the tip 232 of a small injection pipe 226 is important with respect to thorough mixing and suppression of concentration gradients. Generally, tip 232 may be located from about 0.25 to about 0.5 pipe diameters downstream or at a highly preferred distance of from about 0.36 to about 0.39 diameters with about 0.375 diameters being the optimum location.

Figure 4:
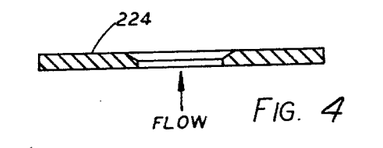
FIG. 4 is a cross-sectional view of a flat plate orifice.

A flat plate orifice which may be utilized in the elbow is shown in FIG. 4. Generally, the orifice diameter is from about 0.7 to about 0.9 of the conduit diameter and may have a small taper (at about 6.0°) leading from the orifice opening. In FIG. 3, orifice 224 is located within a coupling or union, generally indicated by the numeral 310, and connects pipes or conduits 301.

FIG. 4 shows the flat plate orifice in a coupling. Of course, the orifice can be utilized at numerous locations such as tees, elbows and the like or simply in a straight portion of a conduit.

Figure 7:
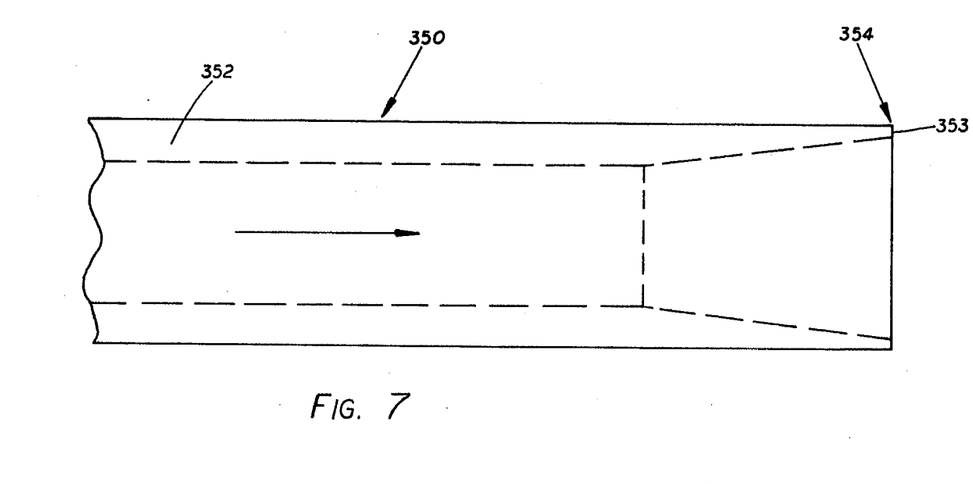
FIG. 7 is a cross-sectional view of a nozzle.

Although the nozzle may generally be a thin pipe or tube, a preferred nozzle is shown in FIG. 7 generally indicated by the numeral 350. Nozzle or distributor 350 generally has a first portion having an average thickness indicated by the numeral 352. The diameter of the nozzle in a second portion proportionally increases until a very thin annulus 353 exists at the tip generally indicated by the arrow 354 of the distributor. The slope of the tapered portion of the distributor is generally less than 7° and preferably about 2° to about 3° on either side. A desirable thickness of the annulus at the tip of the distributor is about 0.01 inches. The diameter, as indicated, generally increases at a proportional rate to accommodate pressure drop of a fluid such as a gas and moreover to ensure good strength and rigidity of the distributor portion. Such a diffuser-tipped distributor also tends to reduce the flow velocity of the gas. Due to the provision of a very thin annulus at the tip of the nozzle, the injected fluid such as a gas is in very close vicinity to the conduit fluid and thereby tends to reduce any eddies as normally encountered with thick walled nozzles. Moreover, additional shearing action is encountered due to the lack of eddies and thus promotes efficient and thorough mixing of the injected fluid as in the vena contracta region of a turbulence-causing device such as a flat plate orifice.

In general, the high turbulence purification or treatment system may be applied to any type of fluid to be treated with a sufficient amount of a second fluid to effect purification. Purification or treatment may be obtained by absorption or high solubility fluids, chemical reaction, or the like and involve detoxification, deodorization, and the like. Additionally, the fluids may either be liquid-liquid, liquid-gas, gas-liquid, or gas-gas.

The high turbulence purification or treatment system is of particular significance with respect to waste or sewage treatment facilities wherein noxious or toxic gases are encountered such as ozone, chlorine, hydrogen sulfide, various organic odors, ammonia and the like. Thus, after sterilization or deodorization, should the fluid to be treated comprise ozone in oxygen or ozone in air, the treating fluid may be an oxidizing agent, a reducing agent, or an absorbing or high solubility fluid agent, as set forth above with respect to their utilization in a cross flow scrubber or washer. Thus, an absorbant compound such as propionic acid could be added through nozzle 308 and emitted in the vena contracta portion downstream from a first flat plate orifice device with further turbulence or mixing occurring at least 25 or more flow conduit diameters downstream as caused by a second flat plate orifice 310. Similarly, as will be apparent to one skilled in the art, other compounds may be added to treat the ozone through nozzle 308. In a similar manner, sulfur dioxide may also be purified.

The invention will be better understood by reference to the following tables which set forth the minimum flow rate required for turbulent flow conditions or thorough mixing. Table I, for a fluid-fluid system wherein the larger length according to either 40 seconds contact time or a transition length of 40 diameters is utilized and similarly in Table II for a gas-liquid system wherein turbulence-causing devices such as flat plate orifices are utilized.

TABLE I

MINIMUM FLOW DESIGN PARAMETERS FOR TURBULENT FLUID-FLUID, INJECTION - MIXING SYSTEMS

| Diameter IN. | 8 | 16 | 24 | 36 | 50 | 60 |
|---|---|---|---|---|---|---|
| Q, cfs (cubic feet per second) | 2.8 | 5.6 | 8.4 | 12.5 | 17.5 | 21 |
| Q, cfm[1] (cubic feet per minute) | 167. | 335. | 502. | 750. | 1050. | 1256. |
| Length, ft.[2] | 320. | 160. | 106. | 70.7 | 51. | 43. |
| Length, ft., mix[3] | 27. | 53. | 80. | 120. | 167. | 200. |
| Velocity, ft. min. | 480. | 240. | 160. | 106. | 77. | 64. |
| Pressure Drop, in. $H_2O$/100 ft. | .06 | .0057 | .0015 | .00038 | .000135 | .000078 |
| Pressure Drop, in. $H_2O$/Inj. Mix | .35 | .11 | .06 | .03 | .01 | .005 |
| Pressure Drop, in. $H_2O$/Contact Total | | | | | | |
| Ozone Req'd gm/hr.[4] | | | | | 12.8 | |
| Oxygen Req'd, cfm[5] | | | | | .11 | |

[1] Based on DV = 64. minimum flow to ensure turbulence, D. inches, V. ft. per sec.
[2] Based on 40 seconds contact time.
[3] Based on 40 D.
[4] Based on 5% ozone in oxygen from ozonator.
[5] Based on 6 ppm ozone from oxygen in air.

TABLE II

CHARACTERISTIC DESIGN PARAMETERS FOR OXYGEN OR AIR, GAS-LIQUID, INJECTION-MIXING SYSTEMS
Note That Data Are For Minimum Capacity to Ensure Turbulent Flow

| Diameter In. | 1 | 2 | 4 | 6 | 12 | 18 |
|---|---|---|---|---|---|---|
| Q min., cfs[1] | .027 | .054 | .108 | .162 | .324 | .486 |
| Q gpm, minimum (gallons per minute) | 12.2 | 24.4 | 48.8 | 73.2 | 146.5 | 219.7 |
| Length, ft.[2] | 200. | 100. | 50. | 33.3 | 16.7 | 11.1 |
| Length, ft., injection-[3] mixing stage | 12.5 | 25. | 50. | 75. | 150. | 225. |
| Velocity Min., Ft. sec.-[1] | 5. | 2.5 | 1.25 | 0.83 | .416 | .28 |
| Air Req'd., $N_2$ sat'n., cfm[4] | .030 | .060 | .12 | .18 | .36 | .54 |
| ($O_3$ at 0.56 ppm) Ozone Feed, lb./day | 0.82 | .16 | .33 | .49 | .98 | 1.5 |
| Oxygen Req'd., $O_2$ sat'n cfm[5] ($O_3$ at 1.25 ppm) | .049 | .098 | .196 | .30 | .60 | 1.20 |
| Ozone Feed, lb./day | .183 | .37 | .73 | 1.1 | 2.2 | 3.3 |
| Pressure Drop, ft., injection-mixing stage | 1.43 | .68 | .15 | .07 | .03 | .005 |
| Pressure Drop, ft., contact stage | 16. | 1.12 | 0 | 0 | 0 | 0 |
| Pressure Drop, ft., total | 17.5 | 1.8 | .15 | .07 | .03 | .005 |

[1] Based on Reynolds Number limitation for turbulent flow, DV = 5.
[2] Based on 40-seconds contact time.
[3] Based on 150 diameters.
[4] Based on 2.5% $O_3$ in air and a dose corresponding to nitrogen saturation which yields an $O_3$ in liquid concentration of 0.56 ppm.
[5] Based on 5% $O_3$ in $O_2$, 40 ppm saturation of oxygen.

Table No. III sets forth data showing the excellent mixing obtained when a turbulence causing device is utilized in a conduit of a fluid-fluid system. In order to determine the extent of mixing, five samples were taken at 30 conduit diameters downstream of the location in the fluid-fluid system where water vapor (gas) was injected into air (gas) in the vena contracta portion of a flat plate orifice. The first location being at a radius wherein the area of the succeeding circle or annulus was equal to one quarter of th total area. The orifice ratio with respect to the conduit diameter was 0.75. The following data were obtained.

TABLE III

Location, R Test/R*

TABLE III-continued

| | | | | | |
|---|---|---|---|---|---|
| Total | 0 | .354 | .61 | .788 | .932 |
| DBT. °C. (dry bulb temp) | 18.2 | 18.2 | 18.2 | 18.2 | 18.2 |
| WBT. °C. (wet bulb temp) | 15.8 | 15.8 | 15.9 | 15.9 | 15.9 |
| Grains 1 lb. | 72. | 72. | 71.1 | 71.1 | 71.1 |
| Comp, ppm. | 10,286 | 10,286 | 10,157 | 10,157 | 10,157 |

*R is the radius location with 0 being the center of the tube

As readily apparant from the above data, very, very small differences in concentration were obtained at various locations along a radius. Additionally, the concentration variation was generally 1% less than the concentration average. This table thus conclusively establishes that excellent mixing is obtained even after a transition length of 30 diameters. This is in comparison with applicant's preferred minimum transition length of 40 diameters which necessarily would give better mixing. Of course, applicant's invention also relates to the incorporation of additional downstream turbulence-causing devices to ensure thorough mixing throughout the system. Moreover, the data establishes that a flat plate orifice having an orifice ratio of 0.75 based upon the conduit diameter establishes good mixing conditions.

In lieu of a conduit having multiple turbulence-causing devices therein, additional embodiments include abruptly changing the diameter of a pipe or flow conduit as well as the provision of a manifold takeoff. Either of these will help to reduce the total system length otherwise required for thorough mixing and hence greatly reduce the physical space required. Considering the abrupt diameter change, a turbulence-causing device such as a flat plate orifice is preferably located in a constant diameter pipe which is connected to a constant diameter pipe or flow channel of a larger diameter. For example, a 4-foot pipe with a flat plate orifice at the end thereof of diameter ratio sufficient to remove the boundary layer fully may be connected to a 7 or 8-foot diameter pipe. Such an orifice at an abrupt change in diameter ensures thorough mixing and hence suppression of any radial concentration gradients. In such a situation, any subsequent downstream turbulence-causing device preferably being at a distance of at least 40 pipe or conduit diameters.

Considering the manifold arrangement, it consists of a pipe or flow conduit which is abruptly converted into several pipes of smaller diameter with a larger overall total conduit flow area if it is desired to maintain the same pressure drop per foot as for the large conduit. For example, a single 4-foot diameter pipe may be abruptly transitioned by manifolding into 24 one-foot diameter pipes. The first turbulence-causing device such as a flat plate orifice is preferably located in each manifold relatively near the conversion from a single pipe into the multiple pipes. According to such an embodiment, the transition length may be reduced from 40 diameters, i.e., 40×4 feet to 40×1 foot, a reduction of 120 feet. Of course, other turbulence-causing devices may be located downstream as before.

Regardless of the type of alternate embodiment in point, the admission of a treating fluid may be carried out in accordance with the above set forth disclosure.

In the conveying of fluid from one area of the system such as a treating portion to another area, the diameter of the flow channels may be changed, as desired. For gradual transitions to decelerate subsonic flow, the diffuser transition should not exceed a taper of approximately 7° to ensure that boundary layer separation is suppressed. This slope is not critical for transition nozzles which accelerate subsonic flow.

Preferably, following a fluid phase treatment station, including downstream mixing as through second or third turbulence-causing devices, a contact chamber may be provided. The purpose of such a chamber is to extend the detention time of the treated fluid after ideal mixing has been developed.

GAS-LIQUID CONTACTING SYSTEMS FOR CHEMICAL REACTIONS

As should be apparent to one skilled in the art, many different types of fluids such as gases may be treated. Moreover, a singular advantage of the in-line reactor or flow conduit for generating chemical reactions involving gas-liquid systems is the amenability to variation in pressure and/or temperature in the pipe line reactor, available in reaction kettles, packed beds or the like.

The basic form of the pipe-line reactor for gas-liquid chemical reactions appears in issued Patents cross referenced herein. In this application, illustrative arrangements and details appear in FIGS. 2, 3, 4, 5 and 7.

Illustrative of industrial processes which are of importance and which involve gas-liquid reactions are the various examples set forth in "Examples of Processes of Industrial Importance where Gas Absorption is Accompanied by Chemical Reaction", Gas-Liquid Reactions, P. V. Danckwerts, F. R. S., McGraw-Hill Series in Chemical Engineering, 1970, which is hereby fully incorporated by reference with respect to the various reactions as well as to the references cited therein. An abstract of this article which sets forth illustrative examples is as follows:

1. $CO_2$, COS, $H_2S$, $Cl_2$
    (i) Absorption of $CO_2$ and $Cl_2$ in aqueous solutions of barium sulphide for the manufacture of $BaCO_3$ and $BaCl_2$, respectively; see Gupta, R. K. and M. M. Sharma: Ind. Chem. Engr. 9 (1967) Trans. 98.
    (ii) Absorption of $CO_2$ in aqueous suspensions of lime for the manufacture of precipitated $CaCO_3$; see Morris, R. H. and E. T. Woodburn: South African Chem. Processing (June–July 1967) CP 88.
    (iii) Absorption of $CO_2$ in aqueous suspensions of MgO for the manufacture of basic $MgCO_3$; see
        (a) Shreve, R. N.: Chemical Process Industries, 3rd Ed., McGraw-Hill, 1967.
        (b) Faith, W.L., D. B. Keyes, and R. L. Clark: Industrial Chemicals, 1965, 3rd ed., John Wiley and Sons, Inc., New York.
    (iv) Absorption of $CO_2$ in aqueous suspensions of CaS; see Chem. Engng. 75 (1968) 94.
    (v) Absorption of $CO_2$ in aqueous solutions of sodium silicate; see Dalmatskya, E. J.: J. Appl. Chem. USSR 40 (1967) 464 (Engl. Trans.).
    (vi) Absorption of $CO_2$ in aqueous solutions of $Na_2S$.
    (vii) Absorption of $CO_2$ in aqueous solutions of potassium carbonate or amines, for removal of $CO_2$ from synthesis gas; see Danckwerts, P. V. and M. M.

Sharma: Chem. Engr. (October 1966) CE 244 (see 10-1).

2. CS$_2$

Absorption in aqueous amine solutions for the manufacture of dithiocarbamates; see Kothari, P. J. and M. M. Sharma: Chem. Engng. Sci. 21 (1966) 391.

3. O$_2$ (i) Absorption of O$_2$ in aqueous solutions of CuCl for conversion to CuCl$_2$ and copper oxychloride; see Jhaveri, A. S. and M. M. Sharma: Chem. Engng. Sci. 22 (1967) 1 (see 10-3).

(ii) Oxidation of Na$_2$SO$_3$ by air or oxygen; used for establishing the characteristics of absorption equipment (see 10-3).

(iii) Air oxidation of acetaldehyde, butyraldehyde, etc., for the production of corresponding acids and acid anhydrides; see (a) Marshall Sittig: Organic Chemical Process Encyclopedia, Noyes Develop. Corp., U.S.A., 1967.

(b) Vrbaski, T., and I. Brihta: Arhiv. Kem. 24 (1952) 111; C.A. 49 (1952) 163.

(c) Kostyck, N. G., Loov, S. V., Falkovski, V. B., Starkov, A. V., and N. M. Levina: Zh. Prikl. Khim. 35 (1962) 2021, J. Appl. Chem. USSR 35 (1962) 1939 (Engl. Trans.).

(iv) Oxidation of cyclohexane to adipic acid; see Steeman, J. W. M., S. Kaasemaker, and P. J. Hoftijzer; 3rd European Symp. Chem. Engng. Chem. Reaction Engng. Oxford, Pergamon Press, 1961, pp. 72–80.

(v) Air oxidation of cumene to cumene hydroperoxide (precursor for phenol); see (a) Low, D. I. R.: Canad. J. Chem. Engng. 45 (1967) 166.

(b) Maminov, O. V. et al.; Khimiya i Tkh. Topliv., Masel (1967) (12), a (Brit. Chem. Eng. Abstract 1968 May, p. 712).

(vi) Air oxidation of toluene to benzoic acid; see Faith, E. L., D. E. Keyes, and R. L. Clark: Industrial Chemicals, 3rd Ed., 1965, John Wiley and Sons Inc, New York.

4. Cl$_2$

A. Addition Chlorination (i) Reaction between Cl$_2$ and C$_2$H$_5$ in C$_2$H$_4$Cl$_2$ medium; see Balasubramanian, S. N., D. N. Rihani, and L. K. Doraiswamy; Ind. Engng. Chem. (Fundamentals) 4 (1965) 184.

(ii) Reaction between Cl$_2$ and C$_3$H$_6$ in C$_3$H$_6$Cl$_2$ medium; see Goldstein, R. F.; Petroleum Chemicals Industries, 2nd Ed., 1958, London, E. & F. N. Spon Limited.

(iii) Reaction between Cl$_2$ and C$_2$H$_2$ to tetrachloroethane; see Marshall Sittig; Organic Chemical Process Encyclopedia, Noyes Develop. Corp., U.S.A., 1967.

(iv) Reaction between Cl$_2$ and trichloroethylene to give pentachloroethane (precursor of perchloroethylene); see Goldstein, R. F.; Petroleum Chemicals Industries, 2nd Ed., 1958, London, E. & F. N. Spon Limited.

B. Subsitution Chlorination (i) Chlorination of a variety of organic compounds such as benzene, toluene (side chain as well as nuclear), phenols, etc. See, e.g. Hawkins, P. A.: Trans. Instn. Chem. Engrs. 43 (1965) T.287.

C. Miscellaneous (i) Reaction of Cl$_2$ with sulfur or sulfur monochloride to give sulfur monochloride and sulfur dichloride.

(ii) Reaction of Cl$_2$ with SO$_2$ to give sulfuryl chloride; see Kirk and Othmer: Encyclopedia of Chemical Technology, Vol. 13, 2nd Ed., 1967, New York, Interscience Publishers, pp. 319, 403.

(iii) Reaction of Cl$_2$ with PCl$_3$ to give PCl$_5$; see Idem., Vol. 10 (p. 477).

(iv) Reaction of Cl$_2$ with FeCl$_2$ to give FeCl$_3$; see Gilliland, E. R., R. F. Baddour, and P. L. T. Brain: A. K. Chem. E. J. 4 (1958) 223 (see 10-2).

5. SO$_3$

Absorption of SO$_3$ in H$_2$SO$_4$ for the manufactur of Oleum; see Duecker, W. W. and J. R. West: The manufacture of sulfuric acid, Reinhold Publishing Corp., New York, 1959.

6. NO$_2$

Absorption in water for the production of HNO$_3$; see (a) Andrew, S. P. S. and D. Hanson: Chem. Engng. Sci. 14 (1961) 105; (b) Kramers, H., M. P. P. Blind, and E. Snoeck; Chem. Engng. Sci. 14 (1961) 115.

7. COCl$_2$

Absorption of COCL$_2$ in alkaline solutions; see Monague, W. H. and R. L. Pigford: A. I. Chem. E. J. 6 (1960) 494.

8. H$_2$

Hydrogenation of a variety of unsaturated organic compounds in the presence of catalysts; see (a) Satterfield, C. N. and T. K. Sherwood: The Role of Diffusion in Catalysis, Addison Wesley, 1963.

(b) DeBoer, J. H. et. al.: The Mechanism of Heterogeneous Catalysis, Amsterdam, Elsevier Publishing Co., 1960.

9. Deuterium

Ammonia-hydrogen process for deuterium separation; see (a) Bourke, P. J. and J. C. Lee: Trans. Instn. Chem. Engrs. 39 (1961) 280.

(b) Bourke, P. J. and D. Pepper: Trans. Instn. Chem. Engrs. 41 (1963) 40.

10. Olefins (i) Absorption of isobutylene in aqueous solutions of H$_2$SO$_4$ for the manufacture of tertiary butanol and for polymerization to di-iso and tri-isobutylene; see Gehlwat, J. K. and M. M. Sharma; Chem. Engng. Sci. 23 (1968) 738.

(ii) Absorption of isobutylene in phenols and substituted phenols in the presence of H$_2$SO$_4$ as a catalyst for the manufacture of the corresponding alkylated products;

(a) DeJong, J. I.: Rec. Trav. Chem. 83 (1964) 469.

(b) Whitney, W.: Ind. Eng. Chem. 35 (1943) 264.

(c) Jelinek, J.: Chem. Prumysl 9 (1959) 398; C.A. 54 (1960) 8696.

(iii) Absorption of butadiene in cuprous ammonium complexes; see Morrell et al., Trans. A. I. Chem. E. 42 (1946) 473.

(iv) Absorption of butenes in sulfuric acid for conversion to secondary butanol; see Rustanov, K. R. and N. M. Chirkov: Zhur. Fiz. Khim. 30 (1956) 261; C.A. 50 (1956) 11081.

(v) Absorption of acetylene in aqueous CuCl solutions to convert it to vinyl acetylene; see Marshall Sittig: Organic Chemical Process Encyclopedia, Noyes Develop. Corp., U.S.A., 1967.

(vi) Absorption of ethylene in benzene to produce ethyl benzene using $AlCl_3$ catalyst; see Marshall Sittig: Organic Chemical Process Encyclopedia, Noyes Develop. Corp., U.S.A. 1967.

(vii) Absorption of acetylene in arsenic trichloride dissolved in $C_2H_2Cl_4$ for the manufacture of chlorovinyldichloroarsine; see Whitt, F. R.: Brit. Chem. Eng. 12 (1967) 554.

(viii) Absorption of ethylene in sulfur mono- or dichloride dissolved in benzylchloride for the manufacture of dichlorodiethysulfide; see Whitt, F. R.: Brit. Chem. Eng. 12 (1967) 554. (Some other examples are also given in this paper).

11. $SO_2$ (i) Absorption of $SO_2$ in aqueous solutions of $NaHSO_3$ and $Na_2SO_3$ in the presence of zinc dust to manufacture dithionite; see Suzuki, E., E. O. Shima, and S. Yagi: Kogyo Kagaku Zasshi 69 (1966) 1841.

(ii) Reduction of $SO_2$ in $SO_3^=/HSO_3^-$—buffer by NaHg amalgam.

(iii) Absorption of $SO_2$ in aqueous solutions of $NaNO_2$ and zinc dust for the manufacture of hydroxylamine.

12. HCl and HBr (i) Absorption of HCl and HBr in higher alcohols for the manufacture of the corresponding alkyl halide (e.g., lauryl alcohol to lauryl chloride or bromide); see Kingsley, H. E. and H. Bliss, Ind. Eng. Chem. 44 (1952) 2479.

(ii) Addition of HBr to alpha-olefins for the manufacture of alkyl bromide (with terminal bromine atom), e.g. methyl undecylenate reacting with HBr.

(iii) Addition of HCl to vinyl acetylene for the manufacture of chloroprene.

We claim:

1. An apparatus for the treatment of a fluid by a treating fluid, comprising;

a flow pipe for a fluid having a Reynolds number of at least 3,000, said flow pipe having a flat plate orifice located therein, a vena contracta portion located in said fluid in said flow pipe at a distance of from 0.25 to 0.5 pipe diameters downstream from said flat plate orifice, the internal diameter of said flat plate orifice ranging from about 0.7 to about 0.9 of the internal diameter of said pipe, a thin injection nozzle means for introducing a treating fluid into said flow pipe, said injection nozzle extending through said flat plate orifice and coaxially located in said pipe, said thin nozzle having a thin tip, said treating fluid flowing through said nozzle tip, said nozzle tip located in said vena contracta portion so that said treating fluid is dispersed into said fluid, said nozzle tip being located at about 0.25 to about 0.5 pipe diameters downstream from said flat plate orifice so that said fluid is thoroughly treated with said treating fluid.

2. An apparatus according to claim 1, wherein said fluid is a gas and said treating fluid is a gas.

3. An apparatus according to claim 1, including a downstream flat plate orifice located at least 40 conduit diameters downstream, said downstream flat plate orifice having a diameter of from 0.7 to 0.9 conduit diameters.

4. An apparatus according to claim 1, including an abrupt change in diameter of said conduit diameter, said abrupt change located downstream from said flat plate orifice.

5. An apparatus according to claim 2, including an abrupt change in the diameter of said conduit diameter, said abrupt change located downstream from said flat plate orifice.

6. An apparatus according to claim 1, including another flat plate orifice located at least 25 conduit diameters downstream, said downstream flat plate orifice having a diameter of from 0.7 to 0.9 conduit diameters.

7. An apparatus according to claim 2, including another flat plate orifice located at least 25 conduit diameters downstream, said downstream flat plate orifice having a diameter of from 0.7 to 0.9 conduit diameters.

8. An apparatus according to claim 6, wherein said nozzle tip is located from about 0.36 to about 0.39 conduit diameters downstream from said flat plate orifice.

9. An apparatus according to claim 7, wherein said nozzle tip is located from about 0.36 to about 0.39 conduit diameters downstream from said flat plate orifice.

10. An apparatus according to claim 6, wherein said nozzle tip has an outwardly tapered portion, said taper being less than 7 degrees.

11. An apparatus according to claim 7, wherein said nozzle tip has an outwardly tapered portion, said taper being less than 7 degrees.

12. An apparatus according to claim 8, wherein said nozzle tip has an outwardly tapered portion, said taper being less than 7 degrees.

* * * * *